United States Patent [19]

Moro et al.

[11] Patent Number: 5,716,790
[45] Date of Patent: Feb. 10, 1998

[54] METHOD FOR ESTIMATING THE LYSINE CONTENT OF SEED BY ELONGATION FACTOR (EF) COMPLEX IMMUNOASSAY

[75] Inventors: Gloverson L. Moro; Jeffrey E. Habben; Brian A. Larkins, all of Tucson, Ariz.

[73] Assignee: Arizona Board of Regents, Tuscon, Ariz.

[21] Appl. No.: 594,109

[22] Filed: Jan. 30, 1996

Related U.S. Application Data

[63] Continuation-in-part of Ser. No. 276,326, Jul. 18, 1994, abandoned.

[51] Int. Cl.[6] .................................................. G01N 33/53
[52] U.S. Cl. ..................... 435/7.9; 435/7.92; 435/7.93; 435/7.94; 435/7.95; 435/975; 436/512; 436/518; 436/548; 530/373; 530/388.5; 530/389.1
[58] Field of Search .................. 435/7.1, 7.9, 7.92–7.95, 435/14, 21, 28, 240.4, 961, 975; 436/512, 518, 528, 531, 541, 548, 808; 530/373, 388.5, 389.1; 47/16.1

[56] References Cited

U.S. PATENT DOCUMENTS 4,704,682  11/1987  Ladner ........................................ 364/496
5,066,595  11/1991  Hubbard et al. ........................ 435/240.45

OTHER PUBLICATIONS

Zhu et al., "A Higher Plant Extracellular Vitronectin–like Adhesion Protein is Related to the Translational Elongation Factor–1α", The Plant Cell, vol. 6, Mar. 1994, pp. 393–404.
Hebben et al., "The Origin of Lysine–Containing Proteins in opaque–2 Maize Endosperm", Plant Molecular Biology, 23: 825–838, 1993.
Aguilar et al., "Two Genes Encoding the Soybean Translation Elongetion Factor eEF–1α are Transcribed in Seedling Leaves", Plant Molecular Biology, 17: 351–360, 1991.

Leuer et al., "Purification and Characterization of Three Elongation Factors, EF–1α, EF–1βγ, and EF–2, from Wheat Germ", The Journal of Biological Chemistry, vol. 269, No. 3, 1984, pp. 1644–1648.
Wallace et al., "New Methods for Extraction and Quantitation of Zeins Reveal a High Content of γ–Zein in Modified opaque–2 Maize", Plant Physiol., (1990) 92, pp. 191–196.
Carvalho et al., "Purification of Various Forms of Elongation Factor 1 from Rabbit Reticulocytes", Archives of Biochemistry and Biophysics, vol. 234, No. 2, 1984, pp. 591–602.
Mertz et al., "Rapid Ninhydrin Color Test for Screening High–Lysine Mutants of Maize, Sorghum, Barley, and Other Cereal Grains", American Assoc. of Cereal Chemists, Inc., vol. 51, 1974, pp. 304–307.
Mertz et al., "Mutant Gene That Changes Protein Composition and Increases Lysine Content of Maize Endosperm", Science, vol. 45, 1964, pp. 279–280.
Damerval et al., "Quantification of Dominance for Proteins Pleiotropically Affected by opaque–2 in Maize", Heredity 70, 1993, pp. 38–51.
Browning et al. "Determination of the Amounts of Protein Synthesis Initiation and Elongation Factors in Wheat Germs. in Wheat Germ." J. of Biol. Chem. 265(29)17967–73,(1990)
Oellenick, M."Enzyme–Immunoassay: A Review." J. Chem. Clin. Biochem. 22:895–904(1984).
Habben et al, "Elongation factor 1α concentration is highly correlated with the lysine content of maize endosperm," Proc. Natl. Acad. Sci. USA 92(19):8640–8644 Sep. 1995.
Habben et al., "Role of Elongation Factor–1α in Determining the Lysine Content of Maize Endosperm," Suppl. to Plant Physiology 108(2):19 abstract #5, Jun. 1995.

Primary Examiner—Carol A. Spiegel
Attorney, Agent, or Firm—Foley & Lardner

[57] ABSTRACT

Seed lysine is detected by an immunoassay in which anti–EF antibody binds seed protein. Seed EF concentration is highly correlated with seed lysine content.

22 Claims, 2 Drawing Sheets

METHOD FOR ESTIMATING THE LYSINE CONTENT OF SEED BY ELONGATION FACTOR (EF) COMPLEX IMMUNOASSAY

This is a continuation in part of U.S. application Ser. No. 08/276,326 filed Jul. 18, 1994 now abandoned.

BACKGROUND OF THE INVENTION

The present invention relates generally to means for the genetic selection of plants and specifically to methods for determining seed lysine content.

Lysine is an essential amino acid in the diets of humans and many economically important animals. But grains such as maize, millet and sorghum contain low concentrations of lysine. As a result, diets comprised of these grains need to be supplemented with extra, usually more expensive sources of lysine.

A major aim of agricultural research has been to improve the nutritional quality of these grains, in particular maize, as summarized by Mertz et al., *Science* 145: 279 (1964), and Nelson, *Adv. Cer. Sci. Tech.* 3: 41 (1980). Maize protein contains 1.5% lysine but the human diet optimally requires 5% of protein to be lysine. Therefore, much research concerns the problem of increasing lysine concentration in maize seeds. Research on improved maize varieties is generally applicable to other grains such as sorghum and millet that have similar endosperm properties and endosperm proteins, as described by Shull et al., *Protoplasma* 171: 64 (1992).

The discovery by Mertz et al., supra, of the high lysine maize opaque2 strain which contains 3% lysine in its protein, stimulated many studies that genetically selected seeds based on their lysine contents. The opaque2 strain lysine concentration was shown to be higher than that of the wild strain because opaque2 seeds contain a lower concentration of the lysine-deficient zein protein fraction and a higher concentration of the lysine-containing non-zein protein fraction from the seed endosperm. Because the opaque2 endosperm is unusually soft and starchy, this so-called "high lysine" maize has not been widely utilized. Continuing development of new strains using "opaque2" modifier genes continues through seed selection based on seed lysine measurements. See "Discovery of high lysine, high tryptophan cereals", in QUALITY PROTEIN MAIZE, Mertz (ed.), pages 1–8, (Am. Assoc. Cereal Chemists, 1992).

The important seed lysine measurement step used in the development of varieties such as the opaque2 strain, however, is slow, expensive and destructive to seed samples. This is because the measurement procedure requires a tedious hydrolysis step followed by amino acid analysis or an indirect measurement via a dye binding assay. See Mertz et al., *Science* 145: 279 (1964), and *Cereal Chem.* 51: 304 (1974), respectively. The lysine measurement procedure also typically requires multiple seeds to generate a sufficient amount of tissue for analysis. This hinders genetic crossing experiments by requiring multiple progeny solely for the lysine determination procedure.

These problems slow down and increase the cost of developing improved higher lysine seeds.

In addition to the measurement of lysine from protein fractions, individual seed proteins and their lysine contents are sometimes measured in different strains of seeds. Damerval, *Heredity* 10: 38 (1993), showed that the higher lysine content of the opaque2 maize strain results from increased amounts of at least six unidentified nonzein polypeptides in the maize endosperm. Similarly, Habben et al., *Plant Molec. Biol.* 23:825 (1993), cloned cDNA that codes for lysine-containing proteins and found higher amounts of elongation factor 1α ("EF-1α"), trypsin inhibitor, catalase 2, RSP 113 and RSP 40 mRNAs in the opaque2 maize strain compared to the wild type strain and relatively unchanged amounts of MRNAS that code for other lysine-containing protein such as sucrose synthase. Of this group, EF-1α protein was found to contain 11% lysine. Aguilar et al., *Plant Molec. Biol.* 17: 351 (1991). SDS-PAGE analysis of other seed endosperm proteins revealed higher amounts of adenosine diphosphate glucose (ADPG) pyrophosphorylase protein in the high lysine opaque2 strain compared to the wild type. Habben et al., supra, at pages 831 and 833. Specific seed proteins are sometimes quantified by immunological methods. For example, see Paiva et al., *Cereal Chemistry* 68: 276 (1991).

There is no suggestion or evidence, however, that individual seed proteins or their mRNAS can be assayed by the techniques summarized above to determine relative seed lysine concentration. Thus, the need remains for a simple and fast method to estimate seed lysine content.

SUMMARY OF THE INVENTION

Accordingly, it is an object of the present invention to provide an improved method for estimating seed lysine content.

Another objective of the invention is to provide a method for the fast and efficient comparison of different seed varieties.

These and other objects are made possible by a simple immunological method for estimating seed lysine content based on the binding of anti-EF complex antibody with seed protein. The method is useful for the genetic selection of new maize, sorghum, millet, wheat, barley, rye, soybean, sunflower, canola and rice varieties and unlike previous methods, only requires one seed per measurement. The method is not limited to the use of intact antibody that binds EF complex for the immunoassay binding step, but can utilize reagents comprised of antibody fragments. Finally, diagnostic test kits are provided in various formats to detect seed lysine.

DETAILED DESCRIPTION OF THE PREFERRED EMBODIMENTS

Figure 1:
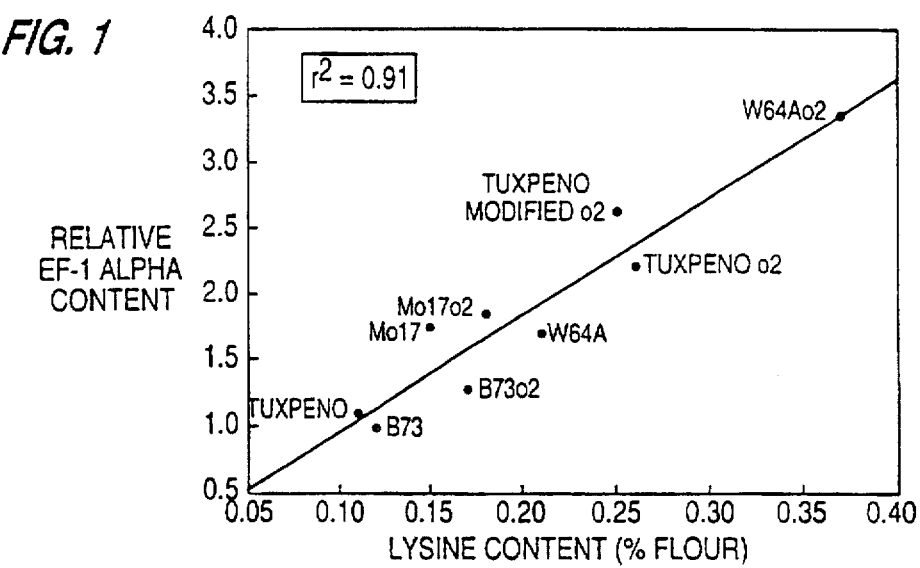
FIG. 1 depicts a regression relationship between EF-1α ELISA measurement and lysine measurements from various maize genotypes.

A significant correlation has been discovered between the immunological measurement of seed EF-1α and seed lysine content. Accordingly, the invention provides for the detection of seed lysine for example, in the context of a breeding program to improve lysine content by the simple measurement of seed EF complex. In this regard, the phrase "EF complex" denotes a component of the cell's protein synthetic machinery which is involved with polypeptide elongation. An EF complex comprises EF-1α, EF-1βγ and EF-2 protein. See Lauer et al., *J. Biol. Chem.* 268: 1644 (1984), which is incorporated in its entirety by reference.

The finding of a high correlation between EF-1α and lysine in seeds is surprising because measurements of two other lysine-containing proteins in seeds, sucrose synthase and ADPG pyrophosphorylase, are not correlated with seed lysine content.

As a result of this finding, lysine content for various seed varieties for the first time can be compared by immunoassay methods. These methods are inherently faster and easier than the procedures heretofore used to measure seed lysine. More specifically, the present invention allows the measurement of EF complex in an aqueous seed extract obtained from as little as one seed.

An EF complex immunoassay according to the present invention is performed by bringing together antibody or antibody binding fragment that recognizes EF complex or a component thereof with seed protein in an immunoassay format to generate a signal in response to the binding of antibody to protein. This signal response reflects the presence of seed lysine.

Seed preparation procedures that solubilize protein can be used to prepare a seed extract for lysine detection. Although various methods that produce protein fractions are suitable, it is especially convenient to prepare a "total protein extract" by grinding frozen or dried seeds to a fine powder with a mortar and pestle or mill and dissolving the proteins in an alkaline buffer that contains sodium dodecyl sulfate and 2mercaptoethanol as taught by Wallace et al., *Plant Physiol.* 92: 191–196 (1990). The solubilized protein is used directly in an immunoassay with dilution in a suitable buffer or alternatively after storage in a solubilized form, frozen form, or precipitated form.

Seed extract is combined with antibody and marker substance in an immunoassay method of the present invention.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of antibodies than bind to EF-1α. "Antibody" also encompasses fragments, like Fv, Fab, Fab', F(ab)₂ and F(ab')₂, of anti-EF-1α antibodies, and conjugates of such fragments, and so-called "antigen binding proteins" (single-chain antibodies) which are based on anti-EF-1α antibodies, in accordance, for example, with U.S. Pat. No. 4,704,692, the contents of which are hereby incorporated by reference. Alternatively, Mabs or a fragment thereof within the present invention can be produced using conventional procedures via the expression of isolated DNA which codes for variable regions of such an Mab in host cells like *E. coli*, see, for example, Ward, et al., *Nature* 341: 544 (1989), or transfected murine myeloma cells. See Gillies, et al., *Biotechnol.* 7: 799 (1989) and Nakatani, et al., *Biotechnol.* 7: 805 (1989).

EF-1α is an abundant protein and has been studied in several species of plants. See Carvalho, et al., *Arch. Biochem. Biophys.* 234: 591 (1984) and Aguilar, et al., *Plant Molec. Biol.* 17:351 (1991). In this description, protein bound by an antibody in accordance with the present invention is denoted "EF-1α," a term used here to encompass any protein having sufficient amino acid sequence similarity with EF-1α to react with antibody raised against EF-1α per se. Included under the EF-1α rubric, for example, is a "vitronectin-like protein," described by Zhu et al., *The Plant Cell* 6: 393 (1994), that has greater than 93% amino acid sequence identity with EF-1α and that is bound by anti-EF-1α antibody.

In the present description, the phrase "marker substance" denotes any molecule that can be conjugated to an antibody and that makes a detectable signal in an immunoassay method. A marker substance can be a catalyst and can be a noncatalytic molecule. An enzyme such as B-galactosidase, alkaline phosphatase or horseradish peroxidase is preferred as a catalyst marker substance, although a non-catalytic marker such as a fluorogenic or chemilumigenic moiety is also suitable.

Immunoassay methods are well known by those of ordinary skill in the art. The basic approach underlying any immunoassay can be adapted for application pursuant to the present invention. The basis of the immunoassay method as used in the present invention is the binding of anti-EF-1α antibody to seed extract. Any assay format that employs such binding is suitable for implementing the invention. For example, the surface may be coated with antibody that binds EF complex.

Heterogeneous format immunoassays are particularly suitable. A preferred format is to immobilize extracted endosperm proteins to a surface. This is followed by contact of the surface with anti-EF-1α antibody. After removal of unbound anti-EF-1α antibody, preferably by washing the surface with buffered solution of detergent, a second antibody-marker substance conjugate is added which binds to anti-EF-1α antibody. After removal of unbound second antibody-marker substance conjugate, preferably by washing the surface with buffered solution of detergent, a signal is produced by the marker substance in proportion to the amount of EF-1α that is bound to the surface.

Homogeneous format immunoassays in which all reactions occur in solution are also suitable. Many homogeneous immunoassay formats such as enzyme modulated immunoassay (EMIT), fluorescence polarization immunoassay and substrate linked immunofluorescence immunoassay are known to those of ordinary skill in the art.

An immunoassay signal result is expressed in any convenient form, such as relative signal response, signal response per unit protein, signal response per unit weight, signal response per seed, etc. For comparing seeds of different strains or species it is preferred to express the immunoassay signal response per unit seed weight.

The present invention, thus generally described, will be understood more readily by reference to the following examples, which is provided by way of illustration and are not intended to limit the present invention.

EXAMPLE 1

EF-1α from Non-Zein Protein Extract

This example illustrates the high correlation between a measurement of protein that are bound by anti-EF-1α antibody and lysine-content measurements performed by conventional amino acid analysis for seeds from a diverse set of maize strains. In contrast, similar measurements of other lysine-containing seed proteins do not correlate with seed lysine measurements.

Endosperm flour from North American normal and opaque2 inbred seeds of W64A, 573, Mo17, and the open-pollinated populations Tuxpeno, Tuxpeno opaque2 and Tuxpeno modified opaque2 from Central America were sampled. Total protein, zein and non-zein fractions were obtained by the method of Wallace et al., supra, and measured by micro-Kjeldahl analysis. AACC: Approved methods of the AACC. Method 46-13. Amer. Assoc. Cereal Chemists, St. Paul, Minn. (1976). Flour samples were extracted for one hour on a shaker at room temperature with 0.0125M sodium borate, pH 10, 1% SDS, 2% 2-mercaptoethanol, at a ratio of 1:10 (flour/solvent). The suspensions were centrifuged at 5000×g for 20 minutes and the supernatants saved. This extraction was repeated twice and the supernatants were pooled.

For total protein analyses, the seed extracts were dried and directly used. For the zein/non-zein determinations, ethanol was added to the total protein extracts to a final concentration of 70%. The mixtures were allowed to stand for two hours with occasional stirring and then centrifuged. The supernatants contained the zein fractions and the pellets contained the non-zein fractions. Total protein, zein, non-zein and residual proteins were analyzed for nitrogen by the micro-Kjeldahl method. Nitrogen values were multiplied by 6.25 to calculate protein amounts. Preliminary testing showed that the presence of sodium dodecyl sulfate did not interfere with nitrogen determination.

Amino acid analyses were obtained by the procedures of sample hydrolysis, performing acid oxidation followed by acid hydrolysis for cysteine, and alkaline hydrolysis for tryptophan. AOAC: Official Methods of Analysis, 15th ed. Method 15:982.30 E(a,b,c). The Association: Washington, D.C. (1990). Amino acids were separated and analyzed using a Beckman 6300 Amino Acid Analyzer equipped with a high performance cation exchange column. Amino acids were detected via a post-column reaction with nonhydrin. Norleucine was used as an internal standard.

For immunoassay measurements, protein extractions and zein/non-zein fractionations were performed as described by Wallace, et al. resuspended i-zein pellets were resuspended in 1 ml of 0.1 N NaOH, 1% SDS and diluted 1000 fold with carbonate coating buffer (Clark et al., in METHODS IN ENZYMOLOGY, Weissbach et al. (eds.) pages 742–766 (Academic Press, 1993). Samples were then serially diluted into wells of an ELISA plate (Immulon2, Immulon4, Dynatech) and incubated overnight at 4° C. Subsequently, excess antigen was removed, the wells were washed with TTBS (25 mM Tris-Hcl pH 7.5, 0.9% NaCl and 0.05% Tween 20 (polyoxyethylene-20-sorbitan monolaurate)) and an antibody specific to EF-1α (Zhu et al., Plant Cell 6: 393 (1994)), sucrose synthase or ADPGase was diluted 1:1000 in TTBS and added to the wells. Sample ELISA plates were incubated for two hours at room temperature. The antibody solutions were removed, ELISA plate wells were washed twice with TTBS and a second antibody conjugated to marker substance, (alkaline-phosphatase-conjugated rabbit anti-chicken; Jackson ImmunoResearch Laboratories, West Grove, Pa.) was diluted 1:4000 in TTBS, and added to the wells. The second binding reaction continued for two hours. The antibody-marker substance solutions were removed and the ELISA plate wells were washed twice with TTBS. Two hundred microliters of alkaline phosphatase substrate reagent (Sigma, St. Louis) made by dilution into diethanolamine substrate buffer (Clark, et al supra) were added to each well. Color from the enzymatic reaction developed for one hour and the absorbencies of the ELISA plate wells were measured on a Dynatech MR700 ELISA plate reader adjusted to 410 nm. The ranges of protein concentrations chosen for the ELISA assays were such that the relationship of absorbance versus relative antigen concentration for each assay was approximately linear as determined by regression analysis.

Figure 2:
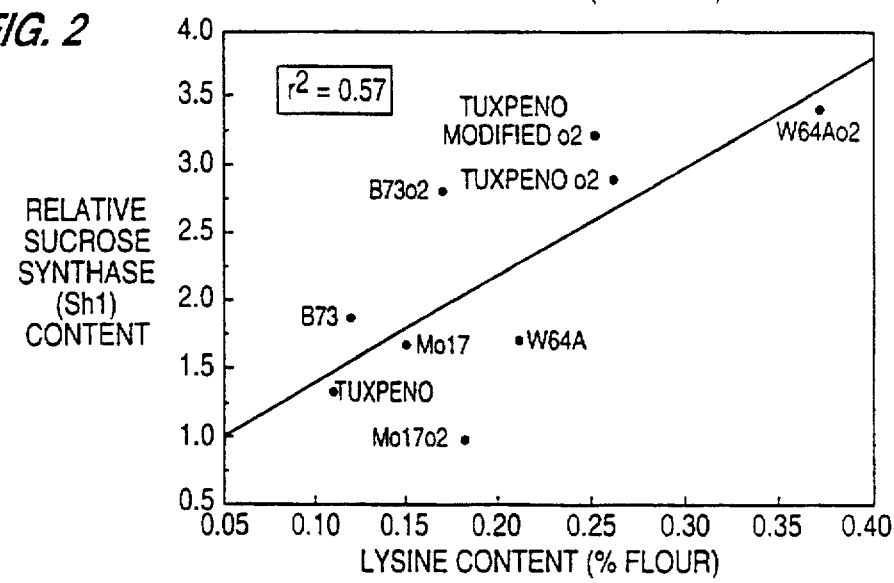
FIG. 2 depicts a regression relationship between Sucrose Synthase measurement and lysine measurements from various maize genotypes.
Figure 3:
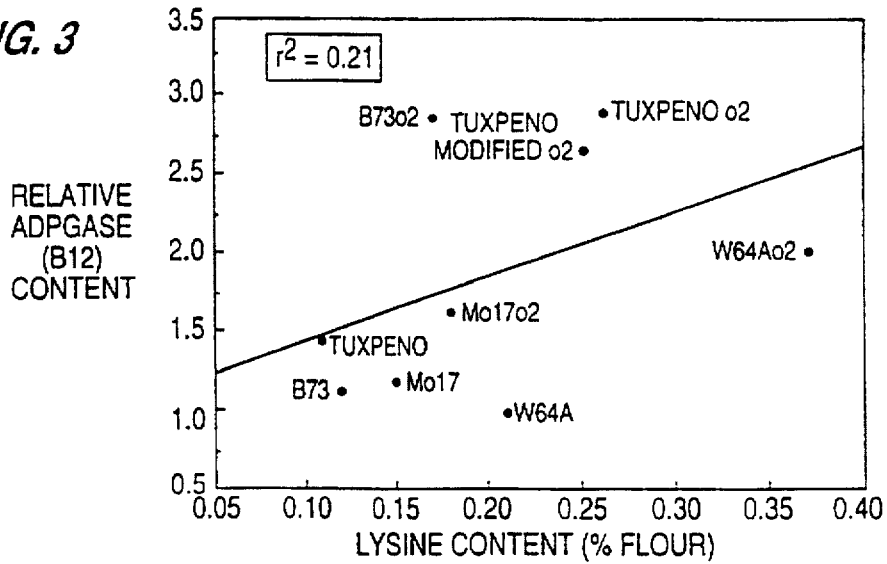
FIG. 3 depicts a regression relationship between ADP-Gase measurement and lysine measurements from various maize genotypes.

FIG. 1 shows that measurements obtained by ELISA with the anti-EF-1α antibody highly correlated (r=0.95) with seed lysine contents. FIG. 2 shows that measurements of seed sucrose synthase contents by ELISA did not highly correlate (r=0.75) with seed lysine contents. FIG. 3 shows that measurements of seed ADPGase contents by ELISA did not highly correlate (r=0.46) with seed lysine contents.

EXAMPLE 2

EF-1α from Total Protein Extract

This example illustrates the high correlation between protein from a total protein extract that is bound by anti-EF-1α antibody, and lysine-content measurements performed by conventional amino acid analysis.

Ten normal inbred strains and their o2 counterparts were selected that represent a wide range of seed lysine contents. Total protein extractions were performed by grinding seeds and solubilization of seed proteins in the alkaline buffer described by Wallace et al., supra. Zein and non-zein proteins were not separated from the total protein extracts. Total protein extracts were diluted 333-fold in carbonate coating buffer as described by Clark et al., Meth. Enz. 118: 742 (1986). Fifty microliters of each dilution were mixed with 100 uL of carbonate coating buffer and placed into a separate well of an ELISA plate. Each sample was then serially diluted and assayed for the presence of EF-1α as described above for Example 1 with the exception that the incubation with anti-EF-1α serum continued for four hours.

Amino acid contents of seeds were determined as described above for Example 1.

Figure 4:
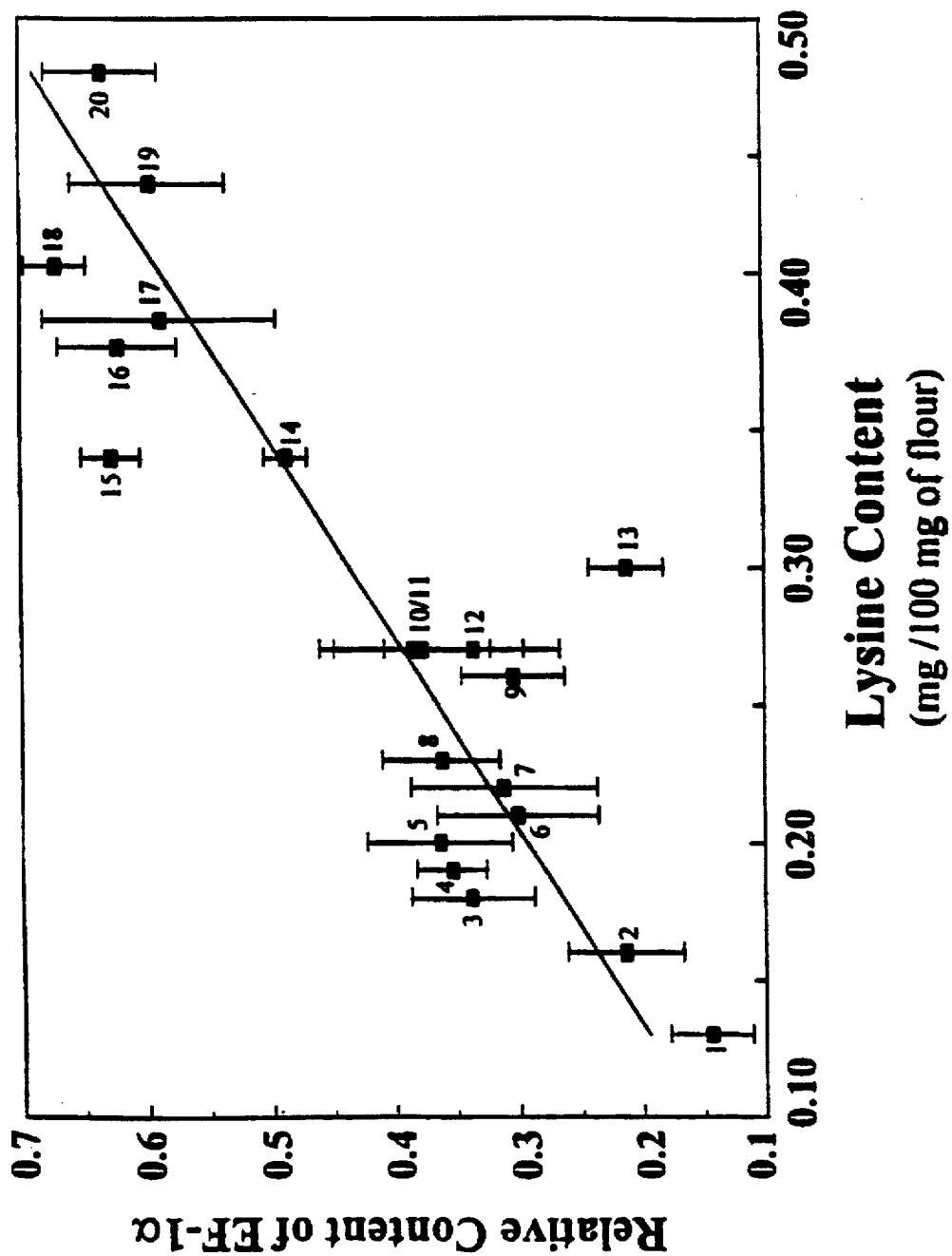
FIG. 4 depicts a regression relationship between EF-1α ELISA measurement of total extracted protein and various maize genotypes.

FIG. 4 shows that measurements of EF-1α from total protein extracts by ELISA highly correlated (r=0.88; P<0.0001) with seed lysine contents. The error bars represent standard deviations about the means.

Although the foregoing refers to particular embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. An immunological method for estimating seed lysine content of a seed sample, comprising the steps of
   (a) contacting a protein extract of the seed sample with antibody that specifically binds elongation factor (EF-1α [EF [-1α]) complex] wherein said antibody is directly or indirectly labeled with a marker substance;
   (b) detecting said antibody bound to EF-1α present in said protein extract to determine the amount of EF-1α present; and
   (c) correlating said amount of EF-1α to the lysine content of said seed sample.

2. The method of claim 1, wherein said protein extract comprises endosperm protein.

3. The method of claim 1, wherein said protein extract is a total protein extract.

4. The method of claim 1, wherein said protein extract is selected from the group consisting of maize seed protein extract, sorghum seed protein extract, millet seed protein extract, wheat seed protein extract, barley seed protein extract, rye seed protein extract, soybean seed protein extract, canola seed protein extract, sunflower seed protein extract and rice seed protein extract.

5. The method of claim 1, wherein said antibody is a monoclonal antibody or a banding fragment thereof.

6. The method of claim 5, wherein said binding fragment is selected from the group consisting of Fv, single-chain antibody, Fab, Fab', F(ab)$_2$ and F(ab')$_2$.

7. The method of claim 1, wherein said antibody is directly labeled with said marker substance.

8. The method of claim 1, wherein said antibody is indirectly labeled with said marker substance.

9. The method of claim 1, wherein said marker substance is selected from the group consisting of β-galactosidase, alkaline phosphatase and horseradish peroxidase.

10. A kit for use in determining seed lysine content of a seed sample, comprising:

(a) a surface that immobilizes a protein extract of said seed sample;

(b) a first receptacle containing a first antibody that specifically binds EF-1α;

(c) a second receptacle containing a conjugate of a second antibody and a marker substance, wherein said second antibody specifically binds said first antibody; and (d) a wash agent for removing unbound protein.

11. The kit according to claim 10, wherein said protein extract is a total protein extract.

12. The kit according to claim 10, wherein said surface is coated with a third antibody that specifically binds EF-1α, wherein said first and third antibodies may be the same or different.

13. The kit of claim 12, wherein said first antibody is a monoclonal antibody or a binding fragment thereof.

14. The kit of claim 13, wherein said binding fragment is selected from the group consisting of Fv, single-chain antibody, Fab, Fab', F(ab)$_2$ and F(ab')$_2$.

15. The kit of claim 10, wherein said first antibody is a monoclonal antibody or a binding fragment thereof.

16. The kit of claim 15, wherein said binding fragment is selected from the group consisting of Fv, single-chain antibody, Fab, Fab', F(ab)$_2$ and F(ab')$_2$.

17. The kit of claim 10, wherein said marker substance is selected from the group consisting of β-galactosidase, alkaline phosphatase and horseradish peroxidase.

18. The kit of claim 10, wherein said wash agent is a buffered solution of detergent.

19. A kit for estimating seed lysine content of a seed sample, comprising:

(a) a surface that immobilizes seed protein extract;

(b) a receptacle containing an antibody-marker substance conjugate wherein said antibody specifically binds EF-1α; and (c) a wash agent for removing unbound protein.

20. The kit according to claim 19, wherein said surface is coated with an antibody that specifically binds EF-1α.

21. The kit of claim 19, wherein said marker substance is selected from the group consisting of β-galactosidase, alkaline phosphatase and horseradish peroxidase.

22. The kit of claim 19, wherein said wash agent is a buffered solution of detergent.

* * * * *